United States Patent
Pettine

(10) Patent No.: US 9,408,874 B2
(45) Date of Patent: Aug. 9, 2016

(54) REGENERATIVE AUTOLOGOUS BONE MARROW CELL THERAPIES AND METHODS FOR THEIR USE IN THE TREATMENT OF JOINT PAIN

(71) Applicant: Kenneth Allen Pettine, Ft. Collins, CO (US)

(72) Inventor: Kenneth Allen Pettine, Ft. Collins, CO (US)

( * ) Notice: Subject to any disclaimer, the term of this patent is extended or adjusted under 35 U.S.C. 154(b) by 0 days.

(21) Appl. No.: 14/180,640

(22) Filed: Feb. 14, 2014

(65) Prior Publication Data

US 2014/0335055 A1 Nov. 13, 2014

Related U.S. Application Data

(60) Provisional application No. 61/765,314, filed on Feb. 15, 2013.

(51) Int. Cl.
*A61K 35/28* (2015.01)
(52) U.S. Cl.
CPC .................... *A61K 35/28* (2013.01)
(58) Field of Classification Search
USPC .................. 435/325; 424/93.7; 623/17.11
See application file for complete search history.

(56) References Cited

U.S. PATENT DOCUMENTS

| 2013/0098827 A1* | 4/2013 | Curran | 210/407 |
| 2014/0099287 A1* | 4/2014 | Murphy et al. | 424/93.7 |
| 2014/0227240 A1* | 8/2014 | Flood | 424/93.72 |
| 2014/0257483 A1* | 9/2014 | Swann | 623/17.11 |

OTHER PUBLICATIONS

Pal R. et al. Effect of Holding Time, Temperature and Different Parenteral Solutions . . . J Tissue Eng Regen Med 2(7)436-444, Oct. 2008.*

* cited by examiner

*Primary Examiner* — Ralph Gitomer
(74) *Attorney, Agent, or Firm* — C. John Brannon; Brannon Sowers & Cracraft PC

(57) ABSTRACT

The present novel technology relates to an autologous cell therapy that comprises a pre-determined amount of a processed bone marrow cellular matrix with a pre-determined amount of pre-mixture, where the pre-mixture includes quantities of anticoagulant solution, dextrose and phosphate buffered saline, and methods for production. The present novel technology further relates to a method of using the composition to reduce discogenic pain in humans.

13 Claims, 5 Drawing Sheets

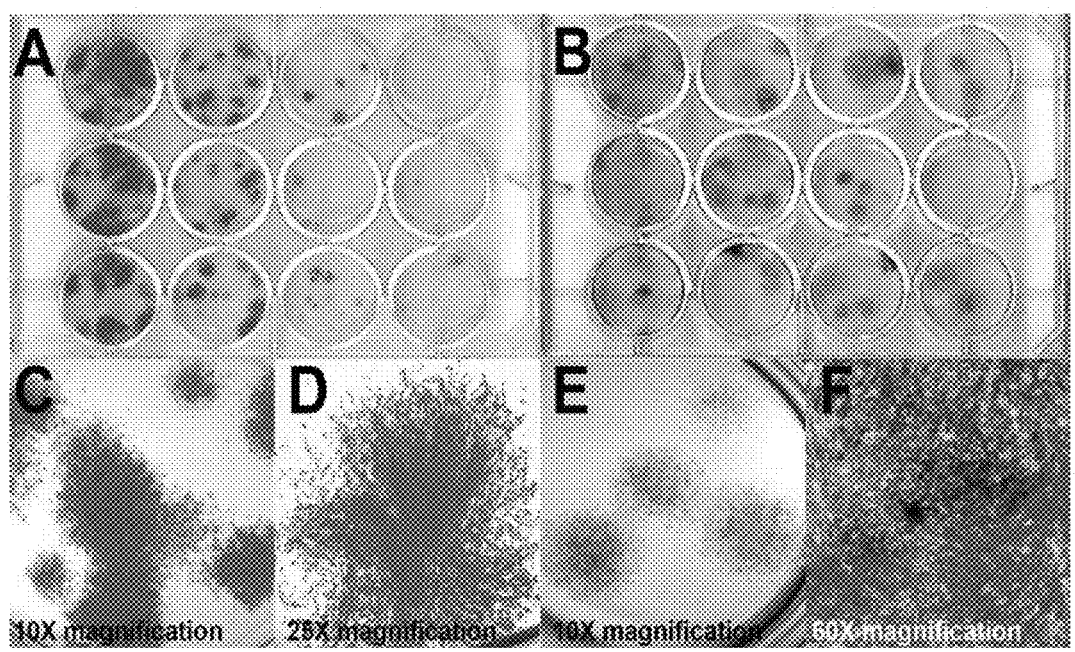
FIG. 1A-F

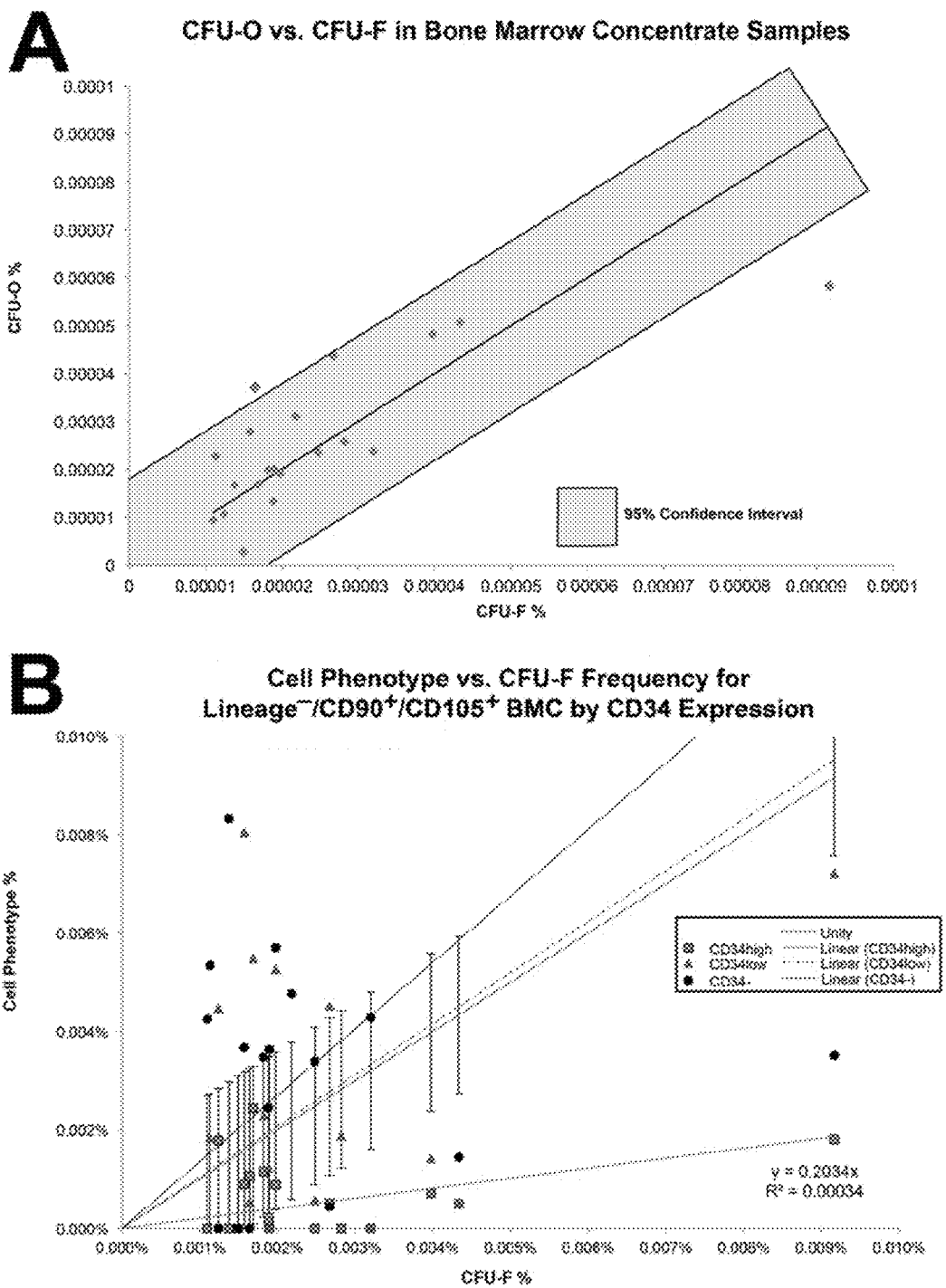
FIG. 2A-B

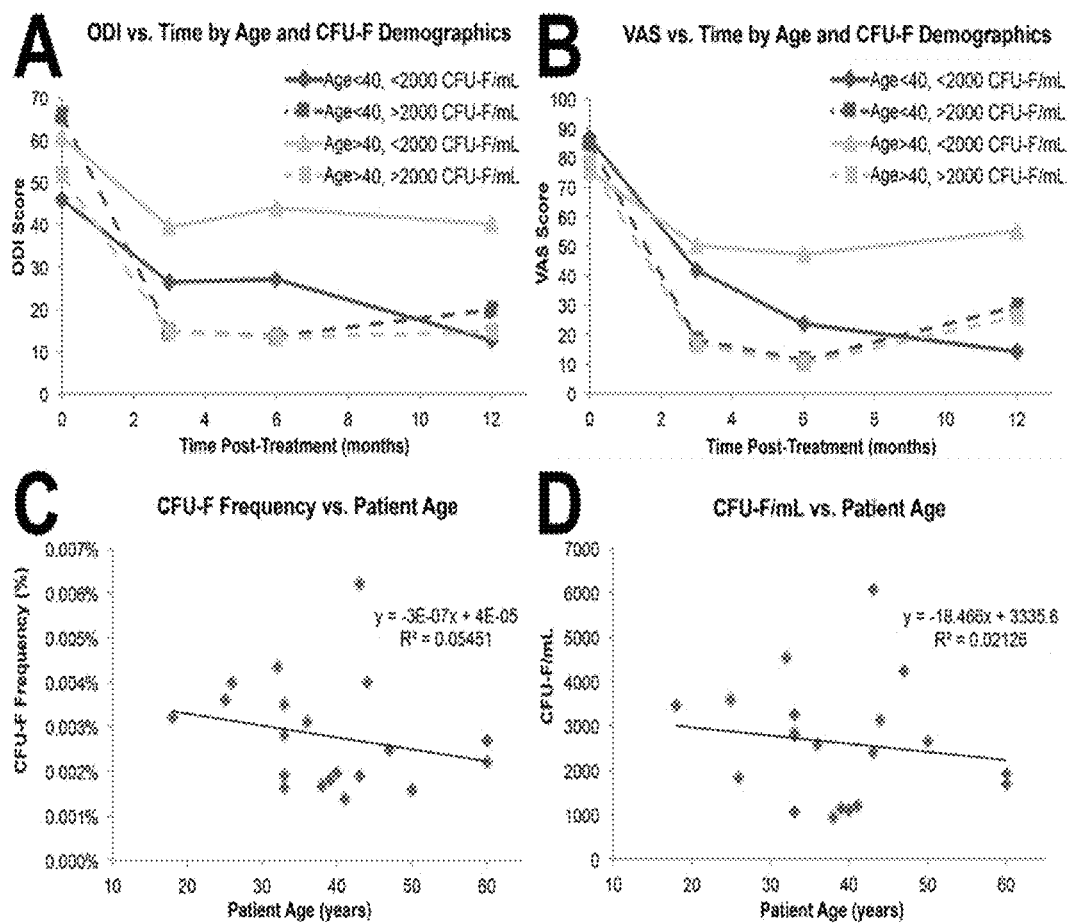
FIG. 3A-D

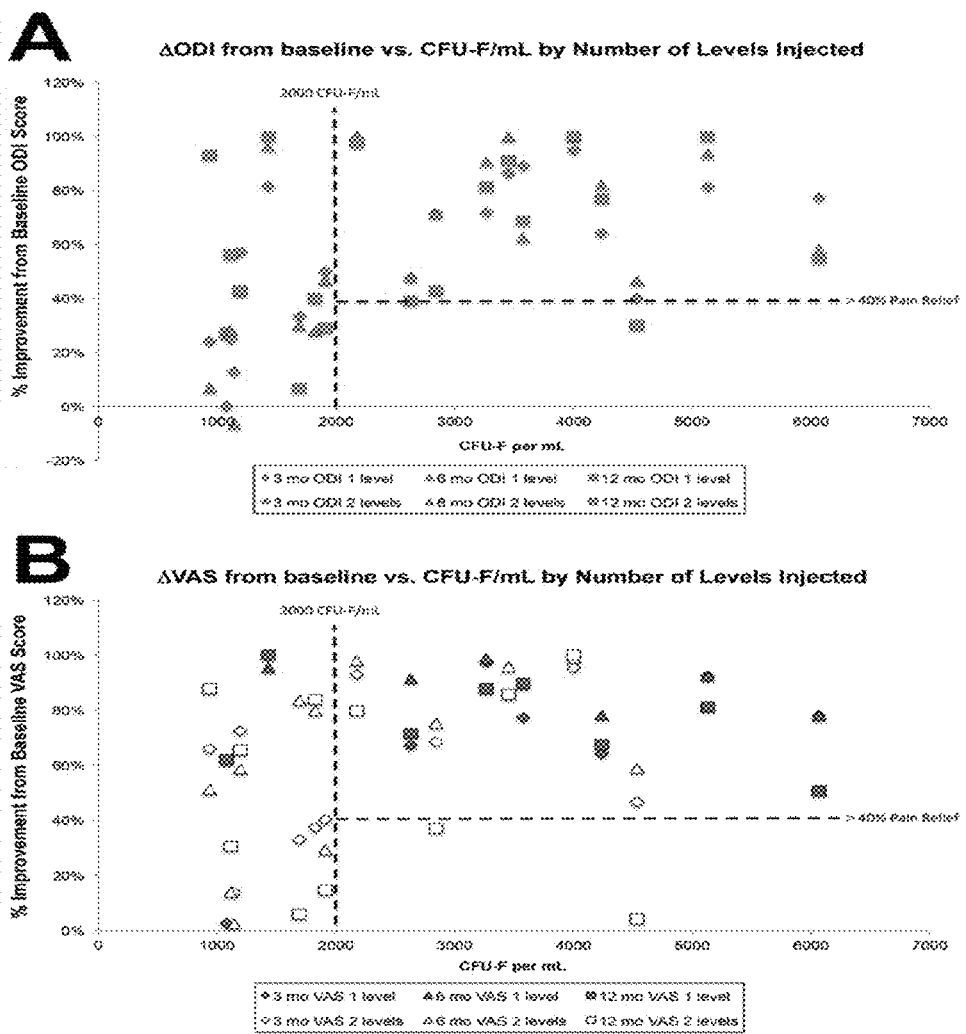
FIG. 4A-B

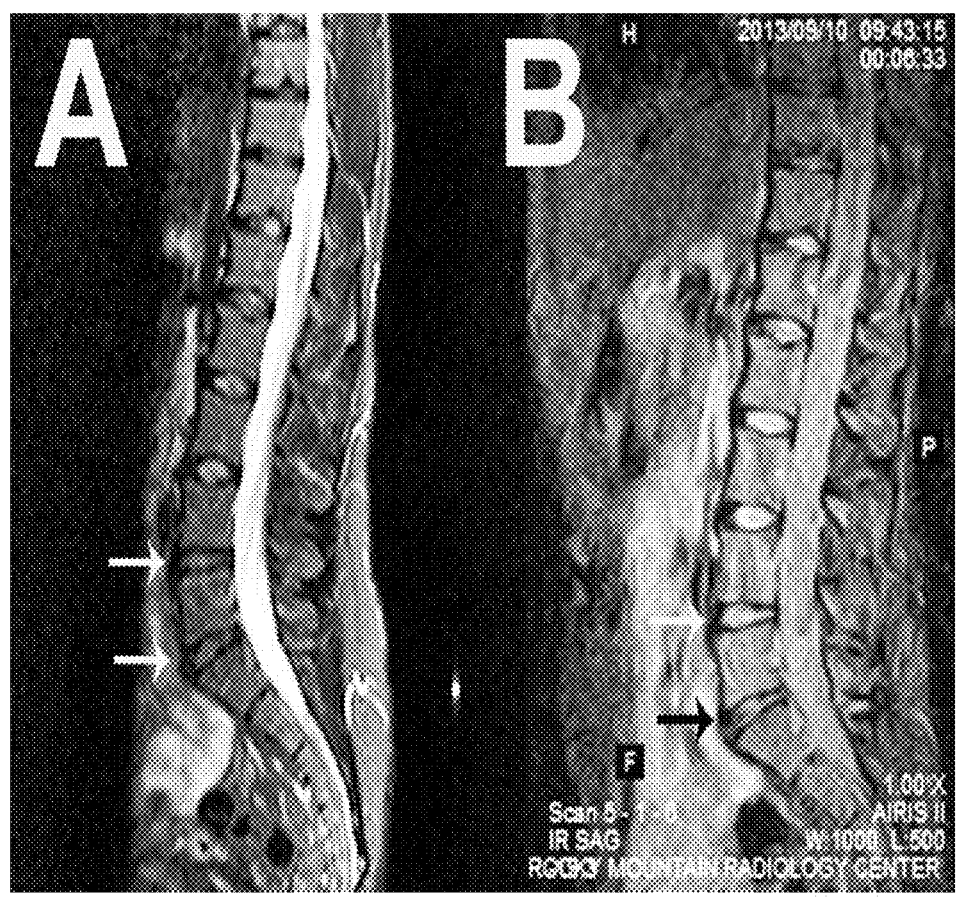
FIG. 5A-B

REGENERATIVE AUTOLOGOUS BONE MARROW CELL THERAPIES AND METHODS FOR THEIR USE IN THE TREATMENT OF JOINT PAIN

CROSS-REFERENCE TO RELATED APPLICATIONS

This utility patent application claims priority to the U.S. provisional application Ser. No. 61/765,314 filed on Feb. 15, 2013.

TECHNICAL FIELD

The present invention relates to cell therapies and more specifically to autologous cell therapies for discogenic pain in mammals.

BACKGROUND

The lumbar intervertebral disc is the largest avascular structure in the human body. A bipedal posture forces the spine into an S-shape curve. The goal is to maintain the skull centered over the pelvis. This has resulted in a lordotic lumbar spine. Degenerative changes in the lumbar discs are typically ubiquitous it is considered a normal part of aging. These degenerative changes have been documented on several MRI scan studies. Gravity creates a compressive load upon the intervertebral discs, and spinal motion creates shear forces and damage from vibration. Mechanical loading cannot in itself explain the ubiquitous degenerative changes seen in the human discs. Various animal studies have been contradictory when it comes to a direct correlation between mechanical stress and disc degeneration. Likewise, human studies attempting to link disc degeneration directly to mechanical factors such as heavy physical work have failed to make a direct correlation.

The cartilage cells living in the avascular lumbar disc receive nutrition through an extracellular matrix with an attenuated supply of nutrients through the vertebral endplates. Nutrients must travel through the capillary network in the intervertebral body and then diffuses through the endplate into the extracellular matrix and finally to the cartilage cells. Calcification of the endplates impairs the flow of nutrients such as glucose and oxygen. Endplate calcification exacerbates the hypoxic acidic environment that greatly impairs the cartilage cell metabolism. The hypoxic acidic environment results in a decrease in proteoglycan synthesis and a cascade of cartilage cell death. The decrease in proteoglycan production is the prevalent feature of disc degeneration. The primary degrading enzyme is the matrix metalloproteinases (MMPs). The MMPs degrade not only the collagens present in the matrix and Aggrecans. Cathepsins are other proteinases associated with disc degeneration that degrade collagen and proteoglycans along with the MMPs. Cathepsins are found more in an acidic pH and may be the primary proteinase in disc degeneration. Degenerated cartilage cells also produce various pro-inflammatory mediators such as leukotriene $B_4$, thromboxane $B_2$, prostaglandin $E_2$, phospholipase $A_2$ and COX-2.

Thus, there remains a need for a point-of-care, autologous cell based therapy that can be implemented with minimal manipulation of the extracted cells and retention of the physiologic regenerative attributes present within the microenvironment of the cellular extract. The present novel technology addresses this need.

BRIEF DESCRIPTION OF THE DRAWINGS

FIG. 1A-F are photo micrographs of prepared BMC in culture as prepared for one embodiment of the novel technology.

FIG. 2A-B are graphical representations of CFU-O and Cell Phenotype, respectively, versus CFU-F frequency in BMC samples as prepared for one embodiment of the novel technology.

FIG. 3A-D are graphical representations of average ODI (A) and VAS (B) scores versus time segregated by patient age and CFU-F concentration in one embodiment of BMC as prepared for one embodiment of the novel technology.

FIG. 4A-B are graphical representations of the improvement of pre-treatment ODI and VAS versus CFU-F concentration in one embodiment of BMC as prepared for one embodiment of the novel technology.

FIG. 5A-B is a T2 weighted Magnetic Resonance Image (MRI) of an area before treatment and 12 months after treatment with one embodiment of the novel technology.

DETAILED DESCRIPTION OF THE INVENTION

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated technology and such further applications of the principles of the novel technology as illustrated therein being contemplated as would normally occur to one skilled in the art to which the novel technology relates.

The use of BMA (bone marrow aspirate) and BMC (bone marrow concentrate) are known to contain hematopoietic as well as mesenchymal cell populations. The novel method of extraction is typically correlative to the source of these cells. Typically, the novel technology utilizes an approach, whereby approximately 10 cc of BMA is drawn with typically frequent rotation and repositioning. Additional draws are done after deeper placement of a needle in the iliac crest.

Typically, the iliac crest, and more typically the posterior iliac crest, is where bone marrow aspirate may be harvested in a surgical setting, however any suitable area where BMA may be extracted may be used. The novel cellular "snapshot' is derived via timely methodologies specific to non-expanded, minimally manipulated, autologous cell and associated endogenous microenvironment ("mileau").

Typically, once extracted, the BMA and the resulting BMC is obtained by isolation of the desired cell populations via centrifugation. However, any suitable means may be used to obtain the BMC from the BMA. When centrifugation is used, the BMA is separated according to the slightly differing specific gravities of the aspirated cell types. The cells contained in the BMA can be stratified under centrifugation. The volume, rate, and time of centrifugation are important for controlling the resulting biologic factors contained within the endogenous mileau.

Typically, the longer the processing time and/or the more agitation and handling, the lower the oxygen level in the extracted cells which typically include cellular constituents and components sequestered in the residual endogenous mileau, wherein the mileau typically includes, antigens, surface biomarkers, proteins and growth factors for angiogenesis, osteogenesis, other regenerative outcomes, and the like.

In some embodiments, the degradative manipulation and resultant influence during processing is limited. The resulting, unadulterated mileau may retain a large number of unchanged biologic drivers, markers and signals that are dose appropriate and specific to the cascade of healing found through the native physiology. The stratification and selection of MSCs and progenitors from this population may influence traits such as specific plasticity and immunomodulation.

Typically, the time between extraction and re-implantation is within 1 hour, and more typically within 30 minutes, and still more typically within 20 minutes. Thus, a point of care approach may be typically implemented with the novel technology.

Optionally, once the BMA has been centrifuged, the resulting stratified cell layers may be prepared for delivery to the patient. Typically, the containers, anticoagulants used, and the delivery media used for interim storage and delivery are also prepared during this step.

In some embodiments, preserving endogenous proteins, structure and morphology resides within this step, as too great a deviation from the oxygen, microenvironment and stress factors can lead to changes in the composition of the mileau. Typically, the proteins, structure, and morphology are not significantly altered.

In one embodiment, the novel delivery media formulation is tailored to preserve the extracted cells and their endogenous factors, while maintaining cell health and identity. Typically, a premixture including an aqueous solution of anticoagulant (ACD-A), an equal amount of dextrose (50%), and phosphate buffered saline (PBS), or the like is pre-mixed and aliquoted in a volume to typically match or approximate the cellular matrix extracted from the centrifugation stratification layers at a ratio of about 1:1. More typically, the premixture is added to the cellular matrix with specific volumes being matched to, or slightly greater than 50/50, by volume, although the ratio may be greater, such as 2:1 or even higher.

The rate of injection of the delivery media may be correlative to the entrapment of oxygen during mixing, which may be beneficial to the cells, as well as minimizing the agitation of the cells and the attached endogenous mileau.

In some embodiments, the steps in extracting, isolating, separating, re-extracting, dosing, mixing, and delivery impact the cell population, endogenous proteins, surface structural and biomarkers, associated with the compositional regenerative capacity. Typically, the shorter the time consumed by the above mentioned steps, the less adulterated the original mileau composition will become.

In another embodiment, the patient's skin is prepped and draped with povidone-iodine to sterilize it. The procedure is performed under fluoroscopic control. The skin is anesthetized with buffered 1% lidocaine using a 27-gauge needle. An 18-gauge needle may be placed under fluoroscopic control into Camden's triangle located just lateral and anterior to the facet joint and posterolateral to the annulus of the disc. A 22-gauge Chiba needle is placed through the 18-gauge needle. Typically, between about 1.5 mL to about 3 mL of bone marrow concentrate are slowly inserted through the 22-gauge Chiba needle into the nucleus at various positions based specifically upon the patient's individual pathology in terms of location of tears in the annulus.

The injection of the autologous cell therapy composition into a joint or disc such as the intervertebral disc (IVD), knee, hip, shoulder, elbow, hand, or any other suitable location is typically correlative to the total volume of the regenerative cell therapy prepared. For example in the case of the IVD, 1-3 cc may be injected into the nucleus pulpous (NP), directly. The typical methodology has the tip of the injection needle advancing into the IVD space, past the mid-line, but in the NP. Upon injection, an aliquoting of the regenerative cell therapy occurs whilst the needle is withdrawn. This retrograde filling approach ensures that the injection of components is spread across the NP and IVD space.

In some embodiments, the ability to rapidly inject the cell therapy affords for improved distribution and engraftment of the media into the surrounding environment which may allow for enhanced distribution of oxygen for all of the cells in the therapy and the residual endogenous growth factors, cytokines and signals to disperse their proteins in order to illicit paracrine and autocrine effects. In the case of the IVD space, where oxygen is low and transport in general is limited, this efficiency typically creates a regenerative healing environment.

In most embodiments, the preservation of endogenous growth factors, signaling molecules, cytokines, and chemokines play a role in creating an efficacious dose of cells and regenerative microenvironmental factors which is a factor in anaerobic, high shear, and/or poorly vascularized environments. If the cells are not surrounded by their mileau, alternate signals and pathways would likely emerge and the regenerative cascade could be underpowered, insufficient, or simply directed down an alternate cellular lineage, resulting in impaired or inefficient regeneration. In most embodiments, if regeneration is not triggered immediately, the chances increase as to an alternate pathway or discouragement of regenerative healing.

Typically, the regeneration of the biochemical balance between the degradation and catabolic destruction of tissues and of the glycosaminoglycan in the IVD and the anabolic production of extracellular matrix (ECM), osmolality and rehydration and structure maintenance of intradiscal pressure is accomplished. In addition to clinical pain and function outcomes as described below, the biomarkers known to correlate to the degenerative process can be used to monitor the reversal of this destructive pathology and the initiation of the regenerative healing cascade. Some specific, though not limited, biomarkers are the fibronectin-aggrecan complex, the Interleukin molecules (IL-1, IL-6, etc. . . . ), as well as tumor necrosis factor alpha (TNF-alpha) as well as presence of MMPs (matrix metalloprotenase), cytokines and chemokines.

In some embodiments, Magnetic Resonance Imaging (MRI) methodologies or the like can track the impact upon the IVD or any other suitable area, namely T1-rho for the assessment of the glycosaminoglycan (GAG) content, proteoglycan degradation, the residual water content, and the like. T2 weighted MRI can be used for determining the degree of IVD degeneration following the Pfirrmann scale.

Typically, the degree of initial disease and degradation is an important factor in determining the appropriate outcome as well as distribution within the physical matrix of the IVD or the like, by virtue of the morphologic and biochemical differences expected in IVD from different degrees of dysfunction or degeneration. Treatment of a Pfirrmann I, II or early III, may not be as impactful as a score of III, IV, V or VI. This may in part be due to the morphologic and biochemical differences within this scale. As the Pfirrmann number increases, the striations of the tissue morphology may increase, the margins between tissue types, become less distinct. Further to this degradation, the biochemical environment becomes more acidic, less oxygenated and biomechanically less favorable to healing.

The expected result from utilization of the novel technology leads to the immediate relief of pain, marked by improvement over pre-treatment by a measurable amount by typically about three months and sustained by typically about 6 months, and more typically to about 12 months. As the data indicate, the VAS pain score improvement may be correlated to improved clinical function as measured by the Oswestry Disability Index (ODI). Additionally, the evidence for the reversal of the degeneration of the disc and the repair of the chemical constituents, proteins, extracellular matrix proteins affording rehydration and natural osmolality of the nucleus puplosis may be realized. This can be seen in FIGS. 5A-B, illustrating a marked improvement in the Pfirrmann score between degenerative disc at pre-operation and at 12 months post-operation. At this point, the patient has been offered a beneficial treatment to a degenerative, painful process likely resulting in surgical intervention. The allowance of more time to pass may offer advantages to the patient and to the ultimate number of treatment options and resulting condition of the underlying tissue and pathology. Demonstrated benefits of the novel system are detailed in the following examples.

EXAMPLE 1

In this example, 60 cc of bone marrow aspirate was collected over ACD-A as needed per process. The final volume of BMC was 2 cc per symptomatic disc. The marrow was processed using the bone marrow concentration system according to the detailed protocol. The patient was given IV antibiotics and placed prone on an image table. Intravenous Versed and Fentanyl was administered and the skin was anesthetized with buffered 1% Lidocaine. The aspirator was rinsed and the syringes were transferred with heparin solution, approximately 1000 U/ml. The heparin solution coated the inner surface of the 60 cc aspiration needle and trephine needle. The remaining heparin was expelled from the syringe. 6 cc of ACD-A was aspirated into the 60 cc syringe. Bone marrow was aspirated from the posterior iliac crest when the patient was positioned prone on a fluoro table. The right iliac wing was prepped and draped according to standard surgical protocols. A trephine needle and 60 cc syringe was used to remove the marrow. The surgeon inserted the trephine needle percutaneously through the skin until the bony surface of the iliac crest was felt. Using a mallet, the needle was then inserted to a depth of 3-4 cm into the crest. This was accomplished with fluoroscopic guidance. A 60 cc syringe containing 6 ml of acid citrate dextrose anticoagulant solution (ACD-A) (10% of the final volume) was attached to the needle. The marrow was aspirated by pulling the plunger back and allowing the syringe to fill to the 10 cc level. The needle was repositioned by advancing 1.5-2 cm and an additional 10 cc of aspirate was obtained. This process was repeated until 60 cc of iliac aspirate was obtained. Once the final marrow volume was reached, the solution was mixed by gentle rocking of the syringe as the syringe was rotated on its long axis. The marrow was then ready for processing. The marrow was mixed anticoagulant solution by gently turning the syringe after each 10 cc of aspirate collection.

The extracted marrow was placed in an isolating canister and loaded into the centrifuge. The marrow was centrifuged for 12 minutes at 3200 rpm. The processed marrow was drawn with a syringe from the centrifuge and then rocked while rotating the syringe on its long axis. The syringe was then presented to a sterile field. The amount of bone marrow concentrate removed from the centrifuge equaled the amount to be injected. The cell delivery media was pre-mixed and aliquoted to 1 cc, composing of 0.5 cc of ACD-A and 0.5 cc of dextrose (50%). The delivery media was injected into a closed vial containing the cell components slowly, in order to homogenize the mixture and incorporate oxygen and turbidity mixing in a closed, sterile system. 2 cc of BMC and 1 cc of delivery media (homogenized) were slowly injected into the symptomatic nucleus utilizing a standard discogram two-needle technique. The post-extraction time was less than 1 hour.

EXAMPLE 2

Pre-treatment Oswestry Disability Index (ODI) and Visual Analogue Scale (VAS) were performed to establish baseline pain scores (average 56.5 and 79.3 respectively), while MRI was independently scored according to the modified Pfirrmann scale. Approximately 1 mL of BMC was analyzed for total nucleated cell (TNC) content, colony forming unit-fibroblast (CFU-F) frequency, differentiation potential, and phenotype characterization.

The average ODI and VAS scores were reduced to 22.8 and 29.2 at 3 months, 24.4 and 26.3 at 6 months, and 25.0 and 33.2 at 12 months, respectively (p≤0.0001). Eight of 20 patients improved by one modified Pfirrmann grade at one year. The average BMC contained $121 \times 10^6$ TNC/mL with 3,019 CFU-F/mL (synonymous with mesenchymal stem cells). Although all subjects presented a substantial reduction in pain, patients receiving greater than 2,000 CFU-F/mL experienced a faster and greater reduction in ODI and VAS. Subjects older than 40 years who received fewer than 2,000 CFU-F/mL experienced an average pain reduction of 33.7% (ODI) and 29.1% (VAS) at 12 months, while all other patients' average reduction was 69.5% (ODI, p=0.03) and 70.6% (VAS, p=0.01).

Bone marrow aspirate (BMA, 55 mL) was collected over acid citrate dextrose-anticoagulant (ACD-A, 5 mL) from the patient's posterior iliac crest. The procedure was performed with IV sedation consisting of Versed and Fentanyl. Positioning of the trephine needle in the iliac wing was confirmed by fluoroscopy. BMA was collected in a 60 mL syringe in a series of discrete pulls on the plunger (targeting a collection of 5-10 mL per pull), with repositioning of the needle tip between pulls based on the reported enrichment of progenitor cells. The BMA was processed using a centrifuge to produce a bone marrow concentrated cell preparation. Typically, a BMC volume of 7 mL (6 mL for injection and 1 mL for cell analysis) was drawn from the processing device.

With the patients in a prone position, the injection site(s) was treated with local anesthetic (1% buffered lidocaine). BMC was percutaneously injected into the symptomatic disc(s) through a standard posterior lateral discogram approach with a two-needle technique. The injection point of the 22 gauge needle was verified with fluoroscopy. Approximately 2-3 mL of BMC was used per symptomatic lumbar disc injection.

Cell analysis and characterization of 20 out of the 26 patients' BMC samples were performed. An aliquot (1 mL) of each subject's BMC was packed in a shipping container with 5° C. cold packs and shipped overnight to the cell analysis laboratory The samples were received and processed immediately to determine total nucleated cell count and viability. The BMC was diluted in phosphate buffered saline with 2% fetal bovine serum and subjected to a gradient separation in order to deplete red blood cells. Analysis of the recovered cells included performing colony forming unit-fibroblast and osteogenic (CFU-F and CFU-O, respectively) assays and phenotypic analysis by flow cytometry. For phenotype analysis, fresh (non-cultured) BMC cells were stained with a series of rabbit anti-human monoclonal antibodies for a hematopoietic lineage-committed (non-progenitor) panel of markers including CD2, 3, 8, and 11b (APC-Cy7), CD34 (PE), CD90 (FITC), and CD105 (APC), as well as appropriate isotype controls. Isotype, single color stain, and four-color stain samples were analyzed. The CFU-F assay was performed by creating a dilution series (in culture medium with 5% FBS and 1% antibiotics) of each cell preparation at concentrations of 50,000 to 500,000 total nucleated cells (TNC) per well in standard 12-well plates. The plates were placed in an incubator at 37° C., 5% $CO_2$ and 100% humidity for 72 hours when the medium was replaced. Medium was replaced every 3 days. After 9 days in culture, wells were gently washed with PBS, fixing the colonies/cells with methanol, staining the attached cells with Crystal Violet, rinsing with water and air-drying the plates. Visualization and counting of the colonies was done with an inverted microscope. Colonies containing 20 or more cells were scored as a CFU-F. The CFU-O assay was performed identically as CFU-F, but after 9 days the medium was changed to an osteogenic induction medium for an additional 9 days with complete medium change every 3 days. On day 18, the wells were washed with PBS, then fixed for 15 minutes in 2% formalin solution and co-stained for alkaline phosphatase activity and calcified extracellular matrix.

Univariable data comparisons (pain scores by time, patient age, number of levels injected, or CFU-F concentration; CFU-F frequency by patient age or CFU-O) were analyzed by two-tailed Student's t-test with a 95% confidence interval (=0.05). Multivariable data were evaluated by analysis of variance (ANOVA) using JMP 9 statistical analysis software (SAS Institute, Cary, N.C.).

Fresh BMC aliquots were analyzed within 24 hours of the procedure. The average TNC concentration, cell viability, CFU-F frequency, CFU-O frequency, and CD marker phenotypic analyses are reported in Table 1. TNC and CFU-F per mL of BMC injectate yields were consistent with published manufacturer's data. The average CFU-O frequency and concentration were slightly higher, but within statistical error compared to CFU-F. All BMC samples yielded robust CFU-F formation after 9 days in culture with a virtually identical yield and frequency of CFU-O. CFU-F and CFU-O stained colonies are illustrated in FIG. 1. Alkaline phosphatase activity is displayed in blue, while mineralization resulted in red coloration of colonies. The statistical correlation between CFU-F and CFU-O is shown in FIG. 2A and demonstrates that 18 of the 20 CFU-O samples analyzed fall within the 95% confidence interval of CFU-F. This indicates that not only do the samples possess a classical characteristic of MSCs (CFU-F in primary in vitro culture), but they also have the capacity to differentiate at nearly a 1-to-1 correlation with CFU-F.

TABLE 1

Average Cell Viability, Total Nucleated Cells (TNC), Total and Frequency of CFU-F/CFU-O and CD Marker Phenotypes in fresh Bone Marrow Concentrate.

| Cell Viability at 24 hours | 98.1 (±1.2) % | TNC/mL in BMC | 121 (±11) × $10^6$ |
|---|---|---|---|
| Cell Phenotype Subpopulation Frequency | % of TNC | Subpopulation Concentration in BMC (cells/mL) | |
| CFU-F | 0.0025% | 3,019 (±491) per mL | |
| CFU-O | 0.0027% | 3,225 (±418) per mL | |
| Lineage$^-$ Cells (CD $2^-/3^-/8^-/11b^-$) | 25.89% | 31.5 × $10^6$ per mL | |
| Lineage$^-$/CD34$^+$ | 1.397% | 1.69 × $10^6$ per mL | |
| Lineage$^-$/CD34$^{High}$/CD90+/CD105+ | 0.0007% | 802 per mL | |
| Lineage$^-$/CD34$^{Low}$/CD90+/CD105+ | 0.0040% | 4,832 per mL | |
| Lineage$^-$/CD34$^-$/CD90+/CD105+ | 0.0049% | 5,914 per mL | |

A substantial fraction of Lineage$^-$ (cells not committed or differentiated toward a hematopoietic lineage) cells were positive for CD90, CD105 and CD34, which are common markers for mesenchymal and hematopoietic stem cells. CD34 expression was observed as three distinct populations: CD34$^{High}$, CD34$^{Low}$, and CD34$^-$. As MSCs have been reported universally to express both CD90 and CD105, the percentages of cells from each of the three CD34 subpopulations that were also Lineage$^-$/CD90$^+$/CD105$^+$ were compared to the CFU-F frequency for each individual BMC sample in an attempt to define a phenotypic population of interest. As listed in Table 2, the average CFU-F frequency was 0.0025%, or approximately 25 per million TNC. The Lineage$^-$/CD34$^{High}$/CD90$^+$/CD105$^+$ population represented only 0.0007% of nucleated cells, while the Lineage$^-$/CD34$^{Low}$/CD90$^+$/CD105$^+$ (0.0040%) and Lineage$^-$/CD34/CD90+/CD105+(0.0049%) populations exceeded the CFU-F frequency and could encompass the MSC population. A linear regression was performed on CFU-F frequency versus Lineage$^-$/CD90$^+$/CD105$^+$ phenotypes by CD34 expression (FIG. 2B). Although none of the populations fit to the CFU-F unity line within statistical error ($R^2>0.9$), the linear fit of Lineage$^-$/CD34$^{Low}$/CD90$^+$/CD105$^+$ most closely matched CFU-F. This method of analysis did not eliminate Lineage$^-$/CD34$^-$/CD90$^+$/CD105$^+$ as a candidate population of CFU-F, as it was within one standard deviation of the CFU-F line for the majority of frequencies.

TABLE 2

Average Pre- and Post-treatment Pain (Oswestry Disability Index, ODI) and QOL (Visual Analogue Scale, VAS, 0-100) Scores. Statistically significant differences from Pre-treatment score: $p \leq 0.0001$ (*), $p < 0.005$ (), $p < 0.01$ (*). Statistically significant differences between compared populations: $p < 0.005$ (#), $p < 0.01$ (##).

| Patient Population | Assessment | Pre-treatment | 3 month | 6 month | 12 month |
|---|---|---|---|---|---|
| All Subjects (n = 26) | ODI | 56.5 | 22.8* | 24.4* | 25.0* |
|  | VAS | 79.3 | 29.2* | 26.3* | 33.2* |
| One-Level Injection (n = 13) | ODI | 56.5 | 18.4* | 19.8* | 26.2** |
|  | VAS | 78.5 | 23.8* | 20.2* | 31.4* |
| Two-Level Injections (n = 13) | ODI | 55.5 | 27.4** | 29.3** | 22.7* |
|  | VAS | 79.4 | 34.8* | 32.7* | 33.0* |
| Age ≤40 (n = 14) | ODI | 57.1 | 18.2* | 20.6* | 25.1** |
|  | VAS | 83.4 | 24.6* | 23.5* | 32.3* |
| Age >40 (n = 12) | ODI | 55.8 | 27.8** | 28.5** | 24.8** |
|  | VAS | 74.8 | 34.2** | 29.2** | 34.5 |
| CFU-F per mL <2000 (n = 9) | ODI | 54.2 | 33.7*** | 36.3 | 26.3** |
|  | VAS | 80.4 | 46.4** | 36.7** | 34.5** |
| CFU-F per mL >2000 (n = 11) | ODI | 59.3 | 14.8*,# | 13.5*,# | 17.6* |
|  | VAS | 82.0 | 17.5*,# | 10.8*,# | 25.5* |

Patients' pain scores were determined by ODI and VAS pain indices prior to treatment and at three, six, and twelve month follow up visits. Data was collected on all enrolled patients. Generally, patients reported moderate discomfort for 24-48 hours after injections followed by relief of pain below baseline values. The average pre- and post-treatment pain scores are reported in Table 2, as an overall series and by population subsets (one-level versus two-level, older or younger than the median age (40 years), and greater or less than 2,000 CFU-F/mL). The average percentage of ODI reduction was 58.1%, 55.5%, and 56.8% after three, six, and twelve months, respectively. Similarly, the average percentage of VAS reduction was 64.6%, 64.2%, and 58.0% after three, six, and twelve months, respectively. Only five patients, three of whom received two-level injections and two who received one-level injections, did not improve by at least 25% in ODI and VAS by three months. Two patients elected to undergo a second injection of BMC at six months and are statistically improved at 12 months. Two single-level injection patients elected to undergo surgery (one anterior lumbar interbody fusion, one posterior two-level fusion) within six months after the BMC injection.

Subjects were divided into subpopulations of interest based on levels (number of discs) injected, age, gender, and CFU-F concentration to determine statistically significant impacts on pain scores. There was no statistical effect of gender on pain score reduction for any sub-divided demographic. Although there was statistically significant reduction in ODI and VAS scores at all post-treatment time points for all demographics (p-values ranging from 0 to 0.01), there were not significant differences in pain scores or percentage of improvement over baseline based on patient age or number of levels injected. The effect of CFU-F (or MSC) concentration on pain relief was statistically significant at three and six months post-therapy (p<0.005 for ODI at three and six months and VAS at three months, p<0.01 for VAS at six months).

As described, there were no statistically significant differences in raw or percentage change of ODI or VAS scores based on age. However, separating cohorts based on both age (≤ or > median age of 40 years) and CFU-F concentrations greater or less than 2,000 per mL of BMC revealed interesting differences in pain relief. Significant overall reduction of ODI and VAS scores (FIGS. 3A and B) was observed in each cohort. As shown in Table 3, all patients with CFU-F concentrations greater than 2,000 per mL in their BMC preparation, regardless of age, demonstrated a statistically significant improvement in pain scores over those below that MSC concentration at three and six months. Interestingly, those differences are greater when the <2,000 CFU-F/mL group is fractionated by age. In younger patients 40 years), there were no significant differences in pain scores at any time point based on CFU-F concentration. For patients >40 years, however, the differences in average ODI and VAS scores between the < or >2,000 CFU-F/mL cohorts were 24.6 (ODI, p=0.01) and 33.4 (VAS, p=0.014) at three months, 30.6 (ODI, p=0.006) and 37.0 (VAS, p=0.02) at six months, and 25.2 (ODI, p=0.025) and 28.8 (VAS, p=0.03) at twelve months. Among all patients with <2,000 CFU-F/mL in their BMC, there was a statistical difference based on age at twelve months (ODI p=0.02, VAS p=0.03). No such difference exists for patients with >2,000 CFU-F/mL. The frequency and concentration of CFU-F by patient are shown in FIGS. 3C and 3D. There was no correlation between age and CFU-F %, but there was evidence of a generally decreasing trend with increased age. There was no significant correlation between CFU-F concentration and patient age due to the variation of CFU-F frequency by patient as well as variation in the TNC concentration.

The statistically significant effects of CFU-F concentration based upon the 2,000 CFU-F/mL threshold were reported in Table 3 and FIG. 3. The seemingly arbitrary 2,000 CFU-F/mL value originated from analysis of percent-wise improvements in ODI and VAS scores versus CFU-F concentration by patient (FIG. 4). Regardless of age, gender, or number of levels injected, all patients who received >2,000 CFU-F/mL reported >40% reduction in ODI and VAS scores at three and six months. Most of these patients (10/11 ODI, 9/11 VAS) sustained >40% pain reduction at twelve months. It should be noted that the patients who dropped below 40% improvement both received a two-level injection. Among patients whose BMC contained <2,000 CFU-F/mL, there was a variation in pain reduction at all time points. There was a mildly significant effect in this population based on age (p≤0.03), but not for number of levels injected.

Physiological changes to injected discs were observed by MRI and scored by a independent reviewer evaluation of images at pre-treatment and twelve months after treatment according to the modified Pfirrmann scale. FIG. 5A-B illustrates representative MRI of L4-L5 and L5-S1 discs prior to and 12 months after BMC injection. Twelve month MRI data show an improvement of at least one Pfirrmann grade in 4 of 10 one-level patients and 4 of 10 two-level patients (Table 3). Six of the 26 patients did not undergo a 12-month MRI (two went on to surgery, four lost to follow-up, three patients in each group). Of the 20 patients whose cells were analyzed, there was an overall average improvement in modified Pfirrmann score of 0.27 and 8 subjects improved one grade from baseline. Based on the cohorts identified by pain scores (CFU-F> or <2,000/mL and patient age > or ≤40 years), similar trends were observed. Patients with BMC containing greater than 2,000 CFU-F/mL, regardless of age, demonstrated an average improvement of 0.58 in modified Pfirrmann and 7 of 12 patients improved by a grade. Younger patients 40 years) with below 2,000 CFU-F/mL also showed improvement, albeit of 0.33 in modified Pfirrmann. Patients older than 40 years with fewer than 2,000 CFU-F/mL demonstrated an overall regression on average of 0.33, although the changes in MRI scores were not statistically significant for any cohort.

whether the patient had a traumatic versus unknown etiology to their discogenic low back pain. Patient age had little effect on pain scores or CFU-F frequency. Although the youngest (18 years) and oldest patient (61 years) had the greatest and least reduction in ODI and VAS, respectively, outcomes were statistically variable, although positive for pain reduction, between ages 25 and 50. However, mesenchymal cell concentration had a tremendous effect on near term (3 month) and sustained (6 and 12 month) pain relief. Comparing patient populations with less than 2,000 CFU-F/mL (n=9) and greater than 2,000 CFU-F/mL (n=11), patients with greater progenitor cell concentrations demonstrated statistically significantly greater improvements in pain scores between treatment and three months and between three and six months. No correlation could be established between CFU-F concentration and patient age due to the inherent variability of CFU-F frequency and TNC concentration between patients While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is

TABLE 3

Pre-treatment and 12 month modified Pfirrmann MRI scores for one-level and two-level intervertebral disc injections by blinded independent reviewer and number of patients who showed improvement of at least one grade among the 20 patients whose BMC samples were analyzed for CFU-F.

| Number of Discs at Corresponding | One Level Injected | | Two Levels Injected | |
|---|---|---|---|---|
| Modified Pfirrmann Grade | Pre-treatment | 12 months* | Pre-treatment | 12 months* |
| Grade 3 | 0 | 0 | 0 | 0 |
| Grade 4 | 2 | 3 | 1 | 2 |
| Grade 5 | 3 | 3 | 8 | 3 |
| Grade 6 | 5 | 1 | 10 | 10 |
| Grade 7 | 3 | 3 | 7 | 5 |

| | Number of Patients with 1 Grade Improvement in Modified Pfirrmann Score |
|---|---|
| All Patients with cell analysis | 8 of 20 |
| All Patients with >2,000 CFU-F/mL | 7 of 11 |
| Patients ≤40 years and <2,000 CFU-F/mL | 1 of 4 |
| Patients >40 years and <2,000 CFU-F/mL | 0 of 5 |

The clinical severity of the 26 patients enrolled should be emphasized (average ODI was 56.5 and VAS was 79.3). All patients enrolled experienced moderate to severe discogenic pain and were surgical candidates for spinal fusion or artificial disc replacement. The patients' pretreatment modified Pfirrmann MRI scores were 4 or greater. The typical patient reported significant relief of their low back symptoms within days following injection of the BMC into the nucleus pulpous of the symptomatic disc(s). The immediate relief may be secondary to a placebo effect and reported anti-inflammatory properties of the MSCs. If a patient's ODI or VAS was not reduced by 25% at the six-month evaluation, the patient was eligible for re-injection of the disc(s) at their and the physician's discretion. Five of the 26 patients met re-injection criteria at six months: two underwent re-injection and are significantly improved clinically at one year; two patients have undergone surgery (one ALIF, one two-level fusion).

The ODI and VAS data obtained at all post-injection time points showed statistically significant sustained pain relief. This data indicated no statistically significant difference in the clinical benefit of the bone marrow concentrate injection understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

I claim:

1. A method for reducing pain in a patient suffering from joint pain, consisting of:
    a) extracting bone marrow to obtain a quantity of bone marrow aspirate;
    wherein a native physiology of the bone marrow aspirate is substantially the same as a native physiology prior to extraction;
    b) centrifuging a quantity of bone marrow aspirate to obtain a quantity of bone marrow concentrate;
    c) mixing the bone marrow concentrate with a premixture to obtain an autologous cell therapy; and d) injecting the autologous cell therapy in a predetermined location at the pained joint on the patient, resulting in a VAS score improvement in the patient by at least 40% after about three months;

wherein the premixture comprises an aqueous anticoagulant solution, a dextrose solution, and a phosphate buffered saline solution; and, wherein the pain is caused by degeneration in the joint or a disease associated with the degeneration.

2. The method of claim 1, wherein the bone marrow aspirate is derived from the posterior iliac crest of the patient.

3. The method of claim 1, wherein the pained joint into which the autologous cell therapy is injected is a degenerated intervertebral disc of the patient.

4. The method of claim 1, wherein time elapsed between step a) and step d) is no more than 60 minutes.

5. The method of claim 3, wherein after injection the degeneration in the disc and a disease associated with the degeneration are arrested, resulting in regeneration of the protein content within the disc.

6. A method for easing pain in a patient suffering from joint pain, consisting of:
   a) extracting a patient's bone marrow to yield a quantity of bone marrow aspirate;
   b) performing a separation on the quantity of bone marrow aspirate to isolate from the bone marrow aspirate a quantity of bone marrow concentrate characterized by a specific desired cell type;
   c) mixing bone marrow concentrate with a premixture to yield a quantity of autologous cell therapy material; and
   d) injecting autologous cell therapy material into a predetermined location at the pained joint on the patient, resulting in a VAS score improvement in the patient by at least 40% after about three months;
   wherein the premixture is selected from the group consisting of aqueous anticoagulant solution, dextrose solution, phosphate buffered saline solution, and combinations thereof; and,
   wherein the pain is caused by degeneration in the joint or a disease associated with the degeneration.

7. The method of claim 6 where in step b), the separation is achieved through centrifugation.

8. The method of claim 6 wherein the pained joint is a degenerated intervertebral disc.

9. The method of claim 6 wherein the time elapsed between step a) and step d) is no more than 60 minutes.

10. The method of claim 6 wherein the time elapsed between step a) and step d) is about 20 minutes.

11. The method of claim 6 wherein in step c), the volume ratio of bone marrow concentrate to premixture is about 1:1.

12. The method of claim 6 wherein in step c), the volume ratio of bone marrow concentrate to premixture is about 1:2.

13. A method for relieving pain in a patient suffering from joint pain, consisting of:
   a) extracting a patient's bone marrow to yield a quantity of bone marrow extract;
   b) stratifying the quantity of bone marrow extract to yield separate strata of bone marrow concentrate characterized by cell types;
   c) selecting one or more desired stratum of bone marrow concentrate;
   d) mixing the selected bone marrow concentrate with a premixture to yield a quantity of autologous cell therapy treatment; and
   e) injecting autologous cell therapy treatment into patient at a predetermined site on the pained joint, resulting in a VAS score improvement in the patient by at least 40% after about three months;
   wherein time elapsed between steps a) and e) is less than about 30 minutes;
   wherein the volume ratio of premixture to selected bone marrow concentrate is between about 1:1 and about 2:1; and wherein the premixture is selected from the group consisting of aqueous anticoagulant solution, dextrose solution, phosphate buffered saline solution, and combinations thereof; and,
   wherein the pain is caused by degeneration in the joint or a disease associated with the degeneration.

* * * * *